(12) United States Patent
Valia et al.

(10) Patent No.: US 9,248,104 B2
(45) Date of Patent: Feb. 2, 2016

(54) TRANSDERMAL METHODS AND SYSTEMS FOR TREATING ALZHEIMER'S DISEASE

(75) Inventors: Kirti H Valia, Plainsboro, NJ (US); Vatsala S Ramaraju, Rochester, MN (US)

(73) Assignee: Core Tech Solutions, Inc., East Windsor, NJ (US)

( * ) Notice: Subject to any disclaimer, the term of this patent is extended or adjusted under 35 U.S.C. 154(b) by 1746 days.

(21) Appl. No.: 11/505,956

(22) Filed: Aug. 17, 2006

(65) Prior Publication Data
US 2008/0044461 A1 Feb. 21, 2008

(51) Int. Cl.
*A61K 31/55* (2006.01)
*A61K 9/70* (2006.01)
*A61K 31/13* (2006.01)

(52) U.S. Cl.
CPC ............. *A61K 9/7053* (2013.01); *A61K 9/7069* (2013.01); *A61K 9/7084* (2013.01); *A61K 31/13* (2013.01)

(58) Field of Classification Search
CPC ................................................ A61K 31/13
USPC ....................................................... 424/449
See application file for complete search history.

(56) References Cited

U.S. PATENT DOCUMENTS

| | | | | |
|---|---|---|---|---|
| 6,352,715 | B1 * | 3/2002 | Hwang et al. | 424/448 |
| 7,220,473 | B2 * | 5/2007 | Beier et al. | 428/40.2 |
| 7,335,379 | B2 | 2/2008 | Carrara et al. | |
| 2002/0192243 | A1 * | 12/2002 | Hsu et al. | 424/400 |
| 2007/0128263 | A1 | 6/2007 | Gargiulo et al. | |
| 2008/0138388 | A1 * | 6/2008 | Aida et al. | 424/448 |

OTHER PUBLICATIONS

Medical News Today (http://www.medicalnewstoday.com/articles/47681.php).*
Exelon Patch (http://www.rxlist.com/exelon-patch-drug.htm).*
Jamakandi VG, Ghosh B, Desai BG, Khanam J. Recent trends in transdermal cardiovascular therapy. Indian J Pharm Sci 2006;68:556-61.*
Barner, E.L., et al., "Donepezil use in Alzheimer's disease", Ann Pharmacother. vol. 32, pp. 70-77 (1998).
Coyle, J.T., et al., "Alzheimer's disease: a disorder of cortical cholinergic innervations", Science. vol. 219, pp. 1184-1190 (1983).
Ghosh, T.K., et al., "Transdermal and Topical Delivery Systems: an Overview and Future Trends in", Transdermal and Topical Drug Delivery Systems 8 (1997).
Hartley, et al., "Delayed rescue of N-methyl-D-aspartate receptor-mediated neuronal injury in . . .", J. Pharmacol. Exp. Ther. vol. 250, pp. 752-758 (1989).
International Search Report for corresponding PCT Application No. PCT/US07/17599, issued Jun. 4, 2008.
Mayeux, R., et al., "Treatment of Alzheimer's disease", N. Engl. J. Med., vol. 341, pp. 1670-1679 (1999).
Meldrum, B., et al., "Excitatory amino acid neurotoxicity and neurodegenerative disease", Trends Pharmacol. Sci., vol. 11, pp. 379-387 (1990).
"Percutaneous Penetration Enhancers" (Eric W. Smith & Howard I. Maibach eds. 1995) (voluminous book).
Physician'S Desk Reference (59th ed., 2005), pp. 1197-1200.
Physician's Desk Reference (59th ed., 2005), pp. 2304-2307.
Reisberg, B., et al., "Memantine Study Group: Memantine in moderate-to-severe Alzheimer's disease", N. Engl. J. Med., vol. 348, pp. 1333-1341 (2003).
Tiseo, P.J., et al.,"Metabolism and administration of 14C-donepezil in healthy volunteers: A single dose study", Brit. J. Clinical Pharmacol., vol. 46 (Supp 1) pp. 25-29 (1998).
Carr, D.B., et al., "Current Concepts in the Pathogenesis of Alzheimer's Disease", Am. J. Med. vol. 103 (3A), pp. 3S-10S (1997).
Choi, D.W., et al., "Aspartate Neurotoxicity on Cultured Cortical Neurons", J. Neurosci. Res. vol. 23, pp. 116-121 (1989).
Ghosh, T. K., et al., "Methods of Enhancement of Transdermal Drug Delivery: Part 2B", Chemical Permeation Enhancers, Pharm. Tech. vol. 17, pp. 68-76 (1993).
Holbrook, K. A., et al., "The Structure and Development of Skin, in, Dermatology in General Medicine", (vol. 1), pp. 97-145 (4th ed., Eds. T. B. Fitzpatrick et al., 1993).
Knopman, D., et al., "Long-term tacrin (Cognex) treatment: Effects on nursing home placement and mortality", Tacrin Study Group, Neurology, vol. 47, pp. 166-177 (1996).
Mattson, M.P., "Neurotransmitters in the regulation of neuronal cytoarchitecture", Brain Res., vol. 13, pp. 179-212 (1988).
Rogers, S.L., et al., "The Pharmacology of a Piperidine Cholinesterase Inhibitor, in, Cholinergic Basis for Alzheimer's Therapy", 314-320 (Birkhauser ed.. 1991).
Wester, R. C., & Maibach, H. I., "Regional Variation in Percutaneous Absorption, in, Percutaneous Absorption . . .", 111-119 (R. L. Bronaugh & H. I. Maibach eds., 2nd ed, 1989).
Moretti, R., et al., "Rivastigmine in subcortical vascular dementia: a comparison trial on efficacy an . . .", Eur. J. Neurol., vol. 8, pp. 361-362 (2001).
Wilcock, G. K., et al., "Efficacy and safety of galantamine in patients with mild to moderate Alzheimer's disease; multicenter . . ." BMJ, vol. 321, pp. 1-7 (2000).

* cited by examiner

*Primary Examiner* — Jake Vu
(74) *Attorney, Agent, or Firm* — Potter Anderson and Corroon LLP

(57) ABSTRACT

Transdermal delivery systems for delivery of Alzheimer's pharmaceuticals, particularly donepezil, over one to seven days are disclosed which deliver the free-base form of the Alzheimer's pharmaceutical at a skin permeation rate such that blood levels of the Alzheimer's pharmaceuticals are comparable to the approved oral dosage forms.

4 Claims, 4 Drawing Sheets

TRANSDERMAL METHODS AND SYSTEMS FOR TREATING ALZHEIMER'S DISEASE

This invention was made with government support under AG017414 awarded by the NIH. The government may have certain rights in the invention.

FIELD

The invention relates to methods and systems for transdermal delivery of Alzheimer's medications.

BACKGROUND

Alzheimer's disease is a neurodegenerative disorder characterized by loss of memory and progressive declining of cognitive abilities. The disorder affects a significant proportion of the aging population. D. B. Carr et al., *Current concepts in pathogenesis of Alzheimer's disease*, 103(3A) AM. J. MED. 3S-10S (1997). Alzheimer's disease's common signs and symptoms include apathy, agitation, mood disturbances, irritability, disinhibition, delusions, aberrant motor behavior, and sleeping and eating abnormalities. Id.

There is much evidence indicating that the memory and attention deficits in patients with Alzheimer's disease are due to degeneration of cholinergic systems that originate in the basal-forebrain-cholinergic system and innervate the neocortex, hippocampus and other brain areas. Coyle et al., 219 SCIENCE 1184 (1983; R. Mayeux et al., *Treatment of Alzheimer's disease*, 341 N. ENGL. J. MED. 1670-1679 (1999).

The first class of drugs approved by the FDA for Alzheimer's treatment were cholinesterase inhibitors. Id. It has been postulated that reversible cholinesterase inhibitors act by selectively inhibiting acetylcholinesterase, the predominate cholinesterase in the brain, thereby increasing the concentration of acetyl choline and enhancing cholinergic function in the central nervous system. S. L. Rogers, et al., *The pharmacology of a piperidine cholinesterase inhibitor, In*, CHOLINERGIC BASIS FOR ALZHEIMER'S THERAPY 314-320 (Birkhauser ed. 1991); P. J. Tiseo et al., *Metabolism and administration of 14C-donepezil in healthy volunteers: A single dose study*, BRIT. J. CLINICAL PHARMACOL. (1998). Oral dosage forms of reversible cholinesterase inhibitors currently available include Aricept® (donepezil hydrochloride), Exelon® (rivastigmine tartrate), Reminyl® (galantamine hydrobromide) and the rarely prescribed Cognex® (tacrine hydrochloride). See e.g., E. L. Barner et al., *Donepezil use in Alzheimer's disease*, 32 ANN PHARMACOTHER., 70-77 (1998); R. Moretti, et al., *Rivastigmine in subcortical vascular dementia: a comparison trial on efficacy an tolerability for 12 months follow-up*, 8 EUR. J. NEUROL. 361-362 (2001); G. K. Wilcock, et al., *Efficacy and safety of galantamine in patients with mild to moderate Alzheimer's disease; multicenter randomized controlled trial*, 321 BMJ 1445-1491 (2000); D. Knopman et al., *Long-term tacrin (Cognex) treatment: effects on nursing home placement and mortality, Tacrin Study Group*, 47 NEUROLOGY 166-177 (1996).

Cortical neurodegeneration in some neuropathies (e.g., stroke, ischemia, etc.) has been attributed to glutamate binding to N-methyl-D-aspartate ("NMDA") receptors, which play a crucial role in glutamate-induced neurodegeneration. Mattson et al., 13 BRAIN RES. 174 (1988); Choi et al., 23 J. NEUROSCI. RES. 116 (1989); Hartley et al., 250 J. PHARMACOL. EXP. THER. 752 (1989); Meldrum et al., 11 TRENDS PHARMACOL. SCI. 379 (1990).

Thus, in addition to the class of acetylcholinesterase inhibitors, Namenda® (memantine hydrochloride) is an oral, non-competitive antagonist of N-methyl-D-aspartate approved by the FDA for treatment of Alzheimer's. B. Reisberg et al., *Memantine Study Group: Memantine in moderate-to-severe Alzheimer's disease*, N. ENGL. MED. 1333-1341 (2003).

Current Alzheimer's treatments are only available in oral dosage form. PHYSICIAN'S DESK REFERENCE 1736, 1197, 2304 (Lori Murray, ed., 59$^{th}$ ed., 2005). A severe disadvantage inherent in such oral dosage forms is patient compliance. Alzheimer's patients often forget or refuse to ingest their medication. Thus, depending on the daily dosage requirements, the assistance of a caregiver may be required multiple times in a single day. For example, the Physicians' Desk Reference states that therapy with the orally administered donepezil should only be started if a caregiver is available to regularly monitor drug intake to avoid abrupt discontinuation of therapy. PHYSICIAN'S DESK REFERENCE 1197 (Lori Murray, ed., 59$^{th}$ ed., 2005).

Of the orally-administered Alzheimer's pharmaceuticals approved by the FDA, Donepezil hydrochloride tablet, or Aricept™, is one of the most prescribed. Donepezil binds to acetylcholinesterase via hydrogen bonding and is easily hydrolyzed by water, thus the duration of enzyme inhibition at the receptor level is very short, and referred to as reversible. Id.

Transdermal delivery systems that provide stable drug blood levels over an extended period (e.g., over a period of days) are advantageous over oral delivery forms because they improve patient compliance. For example, the patient does not have to remember to take the medication or carry pills for administration later in the day. This is particularly applicable to Alzheimer's patients.

But unfortunately, because of the skin's drug penetration resistance, only a limited number of drugs are bioavailable via transdermal administration. T. K. Ghosh, et al., *Transdermal and Topical Delivery Systems: an Overview and Future Trends in*, TRANSDERMAL AND TOPICAL DRUG DELIVERY SYSTEMS 8 (1997).

The skin is a complex multilayer organ with a total thickness of 2-3 mm. The panniculus adiposus, a variably thick fatty layer, is below the dermis. The dermis is a layer of dense connective tissue that supports the epidermis. The epidermis comprises a layer of epithelial cells and is about 100 μm thick. The epidermis is further classified into a number of layers, of which the outermost layer is the stratum corneum (15-20 μm thick). The stratum corneum comprises highly dense, keratinized tissue and is the skin's main source of penetration and permeation resistance. W. Montagna, et al., THE STRUCTURE AND FUNCTION OF SKIN (1974); K. A. Holbrook, K. A. et al., *The Structure and Development of Skin, In*, 1 DERMATOLOGY IN GENERAL MEDICINE, 97-145 (4th ed., Eds. T. B. Fitzpatrick et al., 1993).

Because of the skin's impermeability, in general, only approximately 1 mg of a drug is delivered across a 1 cm$^2$ area of skin in 24 hours. T. K. Ghosh, et al., *Transdermal and Topical Delivery Systems: an Overview and Future Trends in*, TRANSDERMAL AND TOPICAL DRUG DELIVERY SYSTEMS 8 (1997). The higher the molecular weight, the less permeable the drug. Id. Considering the dosage requirements of various drugs, only less than one percent are anticipated to be candidates for transdermal delivery. Id.

What are needed are transdermal delivery systems that can overcome the skin's inherent permeation resistance to deliver Alzheimer's pharmaceuticals over an extended period at plasma concentrations comparable to the oral dosage forms.

SUMMARY

The invention relates to reservoir-type membrane-controlled patches and drug-in-adhesive patches that transdermally deliver Alzheimer's pharmaceuticals to patients over extended time periods at plasma concentrations comparable to the oral dosage forms. The transdermal patches of the invention can continuously transdermally deliver an Alzheimer's pharmaceutical over a period of one to seven days and thus reduce the need for the caregiver supervision that is required for patients on a daily oral prescription.

In one embodiment, reservoir-type patches of the invention comprise a backing film, a drug reservoir, a rate-controlling membrane and an adhesive layer that contacts the skin. The drug reservoir comprises a transdermal Alzheimer's pharmaceutical composition that transdermally delivers an Alzheimer's pharmaceutical through the rate-controlling membrane, into the adhesive layer and then through the human skin for one to seven days or longer.

In another embodiment, reservoir-type patches of the invention comprise a backing film, a drug reservoir, a rate-controlling membrane that contacts the skin. The drug reservoir comprises a transdermal Alzheimer's pharmaceutical composition that transdermally delivers an Alzheimer's pharmaceutical through the rate-controlling membrane, then through the human skin for one to seven days or longer.

In yet another embodiment of the reservoir-type patches of the invention, both the drug reservoir and the adhesive layer comprise an Alzheimer's pharmaceutical. This embodiment reduces the lag time during which the Alzheimer's pharmaceutical would otherwise migrate from drug reservoir into and through the adhesive layer and thus results of faster influx of the Alzheimer's pharmaceutical into the patient's blood stream upon application to the patient's skin.

Another embodiment of the invention comprises a drug-in-adhesive transdermal patch comprising a backing film and a matrix type adhesive layer. The matrix-type adhesive layer contains an Alzheimer's pharmaceutical.

Thus, in one embodiment, the invention relates to a patch comprising a drug reservoir, which drug reservoir comprises an Alzheimer's pharmaceutical, a gelling agent, and a permeation enhancer, and a backing film contacting the drug reservoir, wherein the Alzheimer's pharmaceutical is present in an amount sufficient for transdermal delivery.

In another embodiment, the invention relates to a patch comprising a drug reservoir, which drug reservoir comprises an Alzheimer's pharmaceutical, a gelling agent, and a permeation enhancer, wherein a backing film contacts the drug reservoir, wherein the Alzheimer's pharmaceutical is present in the drug reservoir in an amount sufficient for transdermal delivery, the patch further comprising a matrix type adhesive contacting the drug reservoir, wherein the adhesive also comprises the Alzheimer's pharmaceutical.

In still another embodiment, the invention relates to method of treating Alzheimer's disease comprising transdermally administering a therapeutically effective amount of an Alzheimer's pharmaceutical to a patient in need of such treatment by applying to intact skin of the patient a patch comprising a drug reservoir, which drug reservoir comprises an Alzheimer's pharmaceutical, a gelling agent, and a permeation enhancer, and a backing film contacting the drug reservoir, wherein the Alzheimer's pharmaceutical is present in an amount sufficient for transdermal delivery.

The patches and methods of the invention permit increased patient compliance over the oral dosage forms. In addition, the transdermal patches of the invention reduce the peaks in blood plasma levels that accompany the oral dosage forms. This reduces associated adverse events.

BRIEF DESCRIPTION OF THE SEVERAL VIEWS OF THE DRAWINGS

These and other features, aspects, and advantages of the present invention will become better understood with regard to the following description, appended claims, and accompanying drawings where:

DETAILED DESCRIPTION

1. Definitions

1.1 Alzheimer's Pharmaceutical

Figure 1:
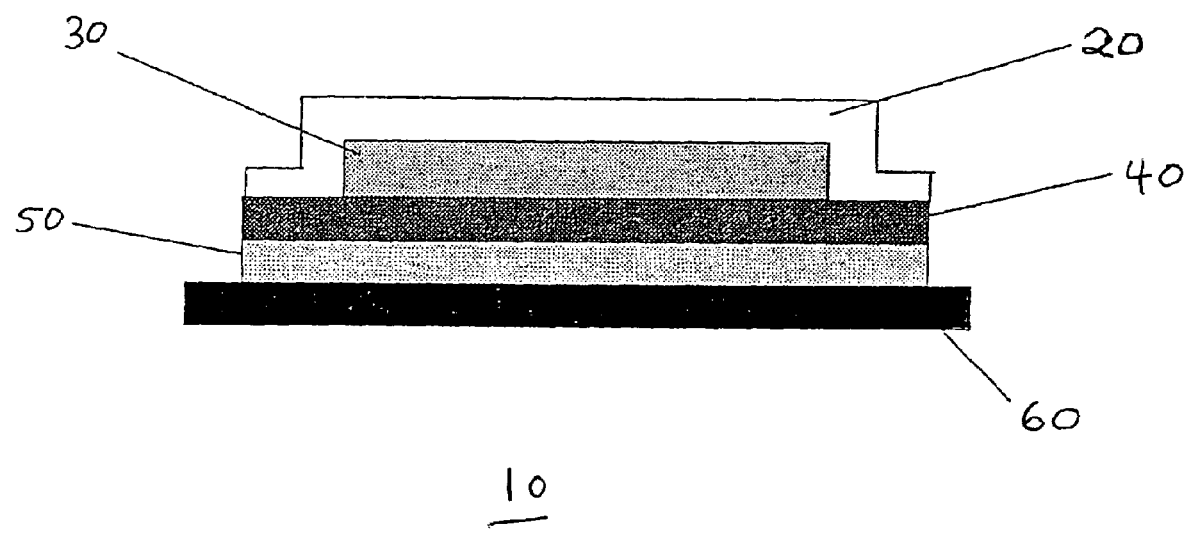
FIG. 1 depicts a drug reservoir patch of the invention.

As used herein, the term "Alzheimer's pharmaceutical" means any drug, medicament, or pharmaceutical useful in the treatment of Alzheimer's disease or a prodrug of an Alzheimer's pharmaceutical and any stereoisomeric forms or mixtures of stereoisomeric forms thereof (e.g., geometrical isomers, enantiomers, diastereomers, racemates, or mixtures thereof).

Preferred Alzheimer's pharmaceuticals for use in the invention contain a basic nitrogen group and are used in patches of the invention in their free-base form. Preferred Alzheimer's pharmaceuticals for use in the invention are approved by the FDA. Preferred Alzheimer's pharmaceuticals are cholinesterase inhibitors, preferably having a molecular weight of from about 100 g/mol to about 800 g/mol, more preferably, of from about 150 g/mol to about 450 g/mol. In another preferred embodiment, the Alzheimer's pharmaceutical is a non-competitive antagonist of N-methyl-D-aspartate. More preferred Alzheimer's pharmaceuticals contain one or more nitrogen atoms in the free-base form. Preferred Alzheimer's pharmaceuticals include, but are not limited to, those compounds listed in Table 1 below, preferably, in their free-base form.

TABLE 1

| | Preferred Alzheimer's pharmaceuticals for Use in the Invention | |
|---|---|---|
| Name | Structure | MW |
| donepezil | 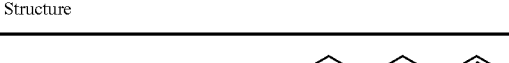 | 379 |

TABLE 1-continued

Preferred Alzheimer's pharmaceuticals for Use in the Invention

| Name | Structure | MW |
| --- | --- | --- |
| rivastigmine | 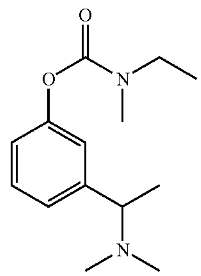 [SMILES: CCN(C)C(=O)Oc1cccc(C(C)N(C)C)c1] | 250 |
| galantamine | 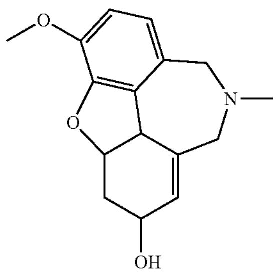 | 287 |
| tacrine | 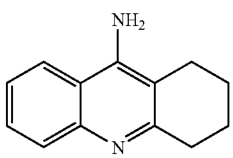 [SMILES: Nc1c2c(nc3ccccc13)CCCC2] | 198 |
| memantine | 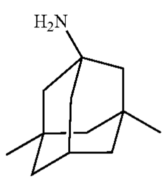 | 179 |

1.2 Mammal

As used herein, the term mammal means any mammal, for example, but not limited to humans; pets, such as dogs and cats; farm mammals, such as horses, cows, pigs, and sheep; and laboratory animals, such as monkeys, guinea pigs, rats, and mice. Preferably, a "mammal" is a human.

1.3 Patch or Transdermal Patch or Transdermal System

As used herein "patch", "transdermal patch" or transdermal system comprises at least a transdermal drug formulation and a backing film, such that, the patch is placed over the application site on a patient's skin to deliver a drug systemically.

1.4 Permeation Rate

As used herein "permeation rate" means the rate at which the Alzheimer's pharmaceutical is delivered through intact, live human skin by way of a patch of the invention and into a patient's blood stream.

1.5 Prodrug

The term "prodrug" refers to a compound that, following administration in a mammal, converts, via biotransformation, into an Alzheimer's pharmaceutical in vivo. Prodrugs are discovered and synthesized using well-known methods, such as those described by 1 BURGER'S MEDICINAL CHEMISTRY AND DRUG DISCOVERY, 172-178, 949-982 (Manfred E. Wolff ed., 5th ed. 1995), hereby incorporated herein by reference.

1.6 Release Rate

As used herein "release rate" means the rate at which the Alzheimer's pharmaceutical is released from a patch of the invention to a surface on which the patch is applied.

1.7 Therapeutically Effective Amount of an Alzheimer's Pharmaceutical

As used herein, a "therapeutically effective amount" with respect to an Alzheimer's pharmaceutical means the amount required in a transdermal system of the invention for transdermal delivery of an Alzheimer's pharmaceutical in blood-plasma concentrations sufficient to treat Alzheimer's disease.

1.8 Transdermal Administration or Transdermal Delivery

As used herein, the term "transdermal administration" or "transdermal delivery" means topical administration of a pharmaceutical to a mammal, to systemically deliver the pharmaceutical through the skin into the mammal's blood stream in an amount sufficient to induce a systemic pharmaceutical effect.

1.9 Transdermally Acceptable

As used herein, the phrase "transdermally-acceptable" means any pharmaceutical, excipient or other component of a transdermal pharmaceutical composition that is safe or approved for transdermal administration in mammals.

1.10 Transdermal Pharmaceutical Composition

The term "transdermal pharmaceutical composition" or "transdermal composition" means a pharmaceutical composition designed for transdermal administration of a drug or pharmaceutical, by way of a transdermal patch.

2. Patches of the Invention

Alzheimer's pharmaceuticals can be transdermally administered by way of patches of the invention to patients for treatment of Alzheimer's disease. Preferably, the patches of the invention are administered to an area of intact skin of from about 5 cm$^2$ to about 100 cm$^1$, preferably of from about 10 cm$^2$ to about 50 cm$^2$ of intact skin over an extended period of time at a permeation rate and an initial two-hour release rate within the ranges set forth below.

FIG. 1 depicts reservoir-type transdermal patch of the invention 10, which comprises backing film 20; drug reservoir 30, which comprises a transdermal Alzheimer's pharmaceutical composition; rate-controlling membrane 40, for controlled delivery of the Alzheimer's pharmaceutical from the drug reservoir; and adhesive layer 50 comprising a pressure-sensitive adhesive. In a preferred embodiment, patch 10 includes protective liner 60. Backing film 20 is configured to provide a central volume which contains a drug reservoir 30 in the form of a gel having an Alzheimer's pharmaceutical therein.

In a preferred embodiment of patch 10, adhesive layer 50 comprises an Alzheimer's pharmaceutical. Thus, in this preferred embodiment, both drug reservoir 30 and adhesive layer 50 comprise an Alzheimer's pharmaceutical. This embodiment reduces the lag time during which the Alzheimer's pharmaceutical would otherwise migrate from drug reservoir 30 into and through the adhesive layer 50 and thus results of faster influx of the Alzheimer's pharmaceutical into the patient's blood stream upon application of patch 10 to the patient's skin.

Figure 2:
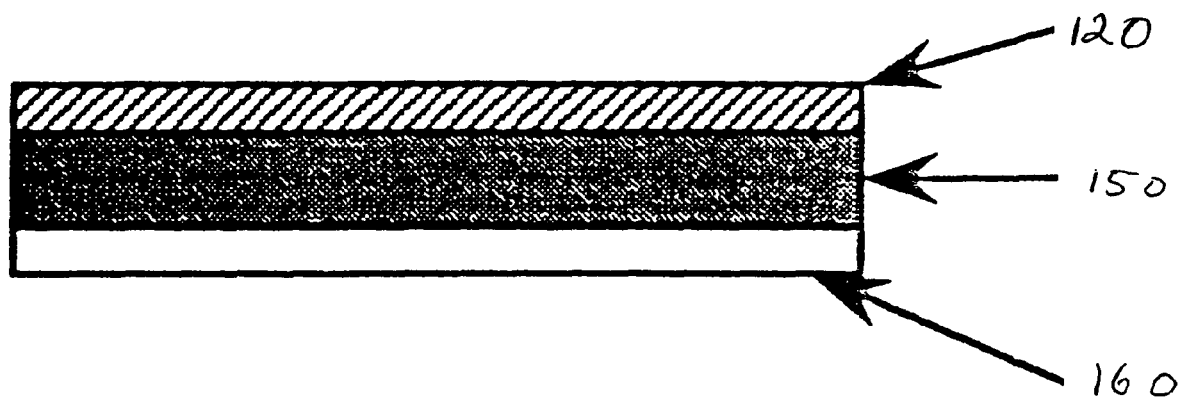
FIG. 2 depicts a drug-in-adhesive patch of the invention.

FIG. 2 depicts drug-in-adhesive transdermal patch of the invention 110, which comprises backing film 120 and adhesive layer 150 comprising a matrix type adhesive and an Alzheimer's pharmaceutical. In a preferred embodiment, patch 110 includes protective liner 160.

Backing film 120 which is impermeable to the Alzheimer's pharmaceutical, protective liner 160 similarly impermeable

| Permeation and Release Rates for Patches of the Invention of 5 cm$^2$ to 100 cm$^2$ | | | | | |
| --- | --- | --- | --- | --- | --- |
| Initial two-hour Release Rate µg/cm$^2$/hour | Preferred Initial two-hour Release Rate µg/cm$^2$/hour | Average Release Rate µg/cm$^2$/hour | Preferred Average Release Rate µg/cm$^2$/hour | Average Skin Permeation Rate µg/cm$^2$/hour | Preferred Average Permeation Rate µg/cm$^2$/hour |
| about 10 to about 250 | about 25 to about 100 | about 2 to about 50 | about 5 to about 20 | about 0.5 to about 20 | about 3 to about 13 |

When so delivered it is possible, by appropriate selection of the surface area of the drug delivery device to obtain total drug input rates which provide an adequate range of titration for individual patient needs while maintaining a safe and effective dosage form.

We have found that there is a relatively wide range of permeability of normal human skin to Alzheimer's pharmaceuticals and this permeability not only varies from individual to individual and site to site but is also highly dependent on the chemical form of the drug. For example, donepezil hydrochloride, the form in which donepezil is presently orally administered, has such a low skin permeability that it is not at all suitable for transdermal delivery even with the use of permeation enhancers. Instead we have found that, in order to obtain the delivery rates noted above, the drug should be incorporated in the transdermal therapeutic system in the form of the free base.

The invention provides transdermal delivery of donepezil in therapeutic amounts for continuous periods from reservoir and matrix type transdermal systems. Preferably, the patches of the invention deliver Alzheimer's pharmaceutical through normal skin into the patient's blood stream in the range of from about 0.5 µg/cm$^2$/hr to about 20 µg/cm$^2$/hr, preferably, of from about 3 µg/cm$^2$/hr to about 13 µg/cm$^2$/hr. In certain embodiments of the invention, sufficient permeation enhancer may be added to the adhesive layer to increase skin permeability.

and adapted to be readily removed from the drug reservoir/contact adhesive layer 150, which consists of a contact adhesive having the Alzheimer's pharmaceutical dissolved in, and if desired, dispersed therethrough. Such a system has the advantage of being easily fabricated, but in the absence of a rate-controlling membrane, delivers drug at a permeation rate which is determined primarily by the permeability of the skin at the site of application on the particular individual.

2.1 The Backing Film

The backing film or backing serves as the upper surface of the patch and functions as the primary structural element and provides the patch with its flexibility. Preferably, the backing film is substantially impermeable to the transdermal pharmaceutical composition. The backing is preferably made of a sheet or film of a flexible elastomeric material. The backing is preferably non-breathable.

Backings for use in patches of the invention are preferably flexible, biocompatible material that imitates the elastic properties of skin and conforms to the skin during movement. Non-occlusive backings allow the area to breath (i.e., promote water vapor transmission from the skin surface), while occlusive backings reduces air/vapor permeation. Preferably, the backing film is occlusive in the reservoir patch of FIG. 1 and in the matrix patch of FIG. 2.

Preferably, the backing film is derived from synthetic polymers like polyolefin oils, polyester, polyethylene, polyvinylidine chloride, and polyurethane. Preferably, the thickness of the backing film is of from about 0.5 mils to about 5 mils, more preferably, 1 to about 3 mils. Preferred oxygen transmissions are from about 2 $cc/m^2/24$ hr to about 100 $cc/m^2/24$ hr, preferably about 70 $g/m^2/24$ hr to about 90 $g/m^2/24$ hr. Preferred MVTR is about 0.3 $g/m^2/24$ hr to about 50 $g/m^2/24$ hr, more preferably about 5 $g/m^2/24$ hr to about 30 $g/m^2/24$ hr.

In a preferred embodiment, the backing film is an occlusive polyester film (commercially available, for example, Scotchpak 9733, 3M Drug Delivery Systems, St. Paul Minn.) of from about 2.0 mils thick 3M Scotchpak 9733 consists of polyester and a medium-density polyethylene/ethylenevinylacetate heat seal layer; the laminate is translucent, conformable, occlusive and heat sealable. This embodiment is useful for the reservoir patch show in FIG. 1.

2.2 Drug Reservoir

The drug reservoir of the reservoir patch shown in FIG. 1 comprises at least an Alzheimer's pharmaceutical and a permeation enhancer. Preferably, the drug reservoir further comprises a gelling agent.

Examples of permeation enhancers for use in drug reservoir systems of the invention include, but are not limited to, ethanol, isopropyl alcohol, and other higher alcohols, such lauryl alcohol, and polyethylene glycol 400, propylene glycol. The preferred permeation enhancer is 95% ethanol USP (5% water), referred to herein as "ethanol 95%". Suitable permeation enhancers are commercially available, for example, from EMD Chemicals, Inc. Gibbstown, N.J.

The amount of permeation enhancer is preferably from about 5% to about 95% by weight of the total drug reservoir weight, more preferably from about 30% to about 80% by weight.

Suitable gelling agents for use in the invention include, but are not limited to, cellulosic polymers, such as hydroxypropylcellulose, hydroxyethylcellulose, and hydroxypropylmethylcellulose. Preferably, the cellulosic polymer is non-ionic and water soluble and its aqueous solutions are unaffected by cations.

The preferred gelling agent is hydroxyethylcellulose. Hydroxyethyl cellulose for use in the invention can be prepared by treating cellulose polymers composed of anhydroglucose units containing three hydroxyl groups with sodium hydroxide and then reacting with ethylene oxide, hydroxyl ethyl groups are introduced to yield a hydroxyl ethyl ether functionality, purifying the reaction product, and grinding into a fine white powder by well-known methods. The preferred hydroxyethylcellulose gelling agent is Natrosol® 250M Pharm, commercially available from Hercules Incorporated, Aqualon Division, Wilmington, Del.

To provide adequate system life, the gel loading is preferably of from about 10 $mg/cm^2$ to about 50 $mg/cm^2$ yielding a dry loading of from about 0.5 $mg/cm^2$ to about 5 $mg/cm^2$. More preferably, the gel loading is of from about 20 $mg/cm^2$ to about 40 $mg/cm^2$. The Alzheimer's pharmaceutical is loaded in the drug reservoir in an amount of from about 0.1% to about 10% of the total gel weight, more preferably, of from about 0.5% to about 5% of the total gel weight.

The compositions of the invention can further comprise one or more additional ingredients, such as one or more thickening agents, medicinal agents or pharmaceuticals, bioadhesive polymers, inert carriers, lipid absorbents, viscosity stabilizers, chelating agents, buffers, anti-fading agents, stabilizers, moisture absorbents, fragrances, colorants, or film-forming materials. One of skill in the art will readily be able to choose such additional excipients based on the physical and chemical properties desired in the final drug reservoir composition. Of course, a single excipient may have multiple functions and properties.

Various drug reservoir compositions can be utilized according to this invention and include both aqueous and non-aqueous systems. A general formulation for the preferred aqueous gel system is shown in Table 2 with the gelling agent being hydroxyethyl cellulose, hydroxpropyl cellulose, or hydroxypropylmethylcellulose.

TABLE 2

| Preferred Drug Reservoir Composition Gel Reservoir Composition (W/W %) | | |
|---|---|---|
| Material | Broad Range | Preferred Range |
| ethanol 95% | 5-95 | 30-80 |
| gelling agent | 1-10 | 1-5 |
| Alzheimer pharmaceutical free Base | 0.1-10 | 0.5-5 |
| water | balance | balance |

2.3 Rate-Controlling Membrane

The rate-controlling membrane of the reservoir patch shown in FIG. 1 permits controlled delivery of the Alzheimer's pharmaceutical from the drug reservoir into the adhesive layer. Rate-controlling membranes for use with patches of the invention are well known in the art and selection is readily accomplished by an ordinary practitioner.

Rate-controlling membranes, useful in the invention include, but are not limited, to thin semi-permeable, ethylene vinyl acetate co-polymer membranes or thin microporous membranes of polyethylene and polyproylene. Suitable rate-controlling membranes are commercially available, for example, from 3M Drug Delivery Systems, St. Paul, Minn.

The rate-controlling membrane can be from about 0.5-5 mils (0.0127-0.1270 mm) thick and preferably about 1-3 mils (0.25-0.076 mm) thick.

In a preferred embodiment, the rate-controlling membrane is a translucent, heat sealable, controlled-caliper ethylene vinyl acetate membrane having a uniform caliper. Preferably, the vinyl acetate content is of from about 0% to about 40%, more preferably, of from about 4% to about 19%, even more preferably of about 9%. Preferably, the MVTR is of from about 15 $g/m^2/24$ hr to about 100 $g/m^2/24$ hr, more preferably, of about 40 $g/m^2/24$ hr to about 60 $g/m^2/24$ hr. Such rate-controlling membranes are commercially available, for example, from 3M Drug Delivery Systems, St. Paul, Minn., i.e., the 3M CoTran® Membranes, preferably, the CoTran® 9702.

2.4 Adhesive Layer

Adhesives for use with patches of the invention are well known in the art and selection is readily accomplished by an ordinary practitioner. Preferably, adhesives useful in the present invention can function under a wide range of conditions such as high and low humidity, bathing, sweating etc. The adhesive is selected depending on the skin-adhesion properties desired, for example, if the patch is a once-a-day, twice-a-week or a once-a-week patch. In a preferred embodiment, the adhesive layer permits the patch of the invention to adhere to the patient's skin for one to seven days.

In a preferred embodiment, the contact adhesive is a matrix-type drug carrier. Matrix-type drug carriers are well known in the art. Suitable matrix-type drug carriers include, but are not limited to polyisobutylene, silicone-based adhesives, and polyacrylate adhesives.

In the drug-in-adhesive patch depicted in FIG. 2, the Alzheimer's pharmaceutical is included directly within the adhesive.

In the drug reservoir patch depicted in FIG. 1, the Alzheimer's pharmaceutical can be included in the adhesive layer or not included in the adhesive layer depending on the delivery properties desired. Preferably, the Alzheimer's pharmaceutical is included directly within the adhesive—in addition to having the Alzheimer's pharmaceutical in the drug reservoir. The loading of the drug in the adhesive layer itself provides a high initial drug release during the lag-time period in which the Alzheimer's pharmaceutical that is in the drug reservoir is migrating through the rate-controlling membrane. The initial release of the Alzheimer's pharmaceutical from the adhesive reduces the time in which the patient attains suitable blood-plasma levels of the Alzheimer's pharmaceutical.

In another embodiment, suitable materials for fabricating of the contact adhesive/reservoir layer include EVA polymers having approximately 0 to 18% vinylacetate content and polyisobutylene/mineral oil containing from 15 to 25% high molecular weight polyisobutelyene (an average molecular weight 1,200,000), 20 to 30% low molecular weight polyisobutelyene (average molecular weight 35,000) and balance of light mineral oil having a viscosity at 38° of approximately 10 centipoise.

In a preferred embodiment, the thickness of the adhesive layer after drying is of from about 0.5 mils to about 12 mils, more preferably, of from about 1 mils to about 4 mils. In another preferred embodiment, the adhesive layer has a weight of from about 5 mg/cm$^2$ to about 50 mg/cm$^2$, more preferably, of from about 10 mg/cm$^2$ to about 30 mg/cm$^2$.

In one embodiment of the FIG. 2 drug-in-adhesive patch, the Alzheimer's pharmaceutical is included in the adhesive layer in an amount of from about 0.01 mg/cm$^2$ to about 10 mg/cm$^2$, more preferably of from about 0.2 mg/cm$^2$ to about 4 mg/cm$^2$.

In one embodiment of the FIG. 1 reservoir patch, if the Alzheimer's pharmaceutical is included in the adhesive layer, its content in the adhesive layer is of from about 0.01 mg/cm$^2$ to about 10 mg/cm$^2$, more preferably of from about 0.2 mg/cm$^2$ to about 4 mg/cm$^2$.

In another embodiment of the reservoir patch depicted in FIG. 1, preferably, the Alzheimer's pharmaceutical is present in the adhesive layer in an amount such the patient's skin is saturated with the Alzheimer's pharmaceutical during the first two hours after application of the patch, herein referred to as a burst effect. Preferably, the initial two-hour release rate is of from about 10 μg/cm$^2$/hour to about 250 μg/cm$^2$/hour, more preferably, of from about 25 μg/cm$^2$/hour to about 100 μg/cm$^2$/hour. This allows the patient to obtain suitable blood plasma levels of the Alzheimer's pharmaceutical within the first two hours of application.

Preferably, the adhesive is a composition is amine-resistant silicone; natural or synthetic rubber; a polyacrylate such as, polybutylacrylate, polymethylacrylate, poly-2-ethylhexyl acrylate; polyvinylacetate; polydimethylsiloxane, polyisobutylene (PIB); and combinations thereof.

Suitable polyisobutylene contact adhesives include polyisobutylene/mineral oil containing from 15 to 25% high molecular weight polyisobutelyene (an average molecular weight 1,200,000) 20 to 30% low molecular weight polyisobutelyene (average molecular weight 35,000) and balance of light mineral oil having a viscosity at 38° C. of approximately 10 centipoise.

A preferred adhesive is silicone medical adhesive Bio PSA 7-4301, commercially available from Dow Corning Corporation, Midland, Mich.

Permeation enhancers that may be included in the adhesive compositions to optimize transfer of the Alzheimer's pharmaceutical through the stratum corneum and into the blood stream. For a discussion of use of permeation enhancers in topical formulations see generally, PERCUTANEOUS PENETRATION ENHANCERS (Eric W. Smith & Howard I. Maibach eds. 1995); Ghosh, T. K. et al. 17 PHARM. TECH. 72 (1993); Ghosh, T. K. et al. 17 PHARM. TECH. 62 (1993); Ghosh, T. K. et al. 17 PHARM. TECH. 68 (1993), all of which citations are hereby incorporated herein by reference. The permeation enhancer should be pharmacologically inert, non-toxic, and non-allergenic, have rapid and reversible onset of action. Examples of permeation enhancers for use in adhesives of the invention include, but are not limited to, higher alcohols, lauryl alcohol, salicylic acid, octolyphenylpolyethylene glycol, polyethylene glycol 400, propylene glycol, N-decylmethylsulfoxide (n-DMS), polyethylene glycol monolaurate, dilaurate and related esters, glycerol monooleate and related mono, di and trifunctional glycerides, diethyl toluamide, Azone®, N,N-dimethyllauramide, N,N-dimethyl lauramine oxide, methylaurate, lauryl lactate, isopropyl myristate, linoleic acid, Ceraphyl® 31, and the like.

TABLE 3

Preferred Drug-in-Adhesive Compositions
Preferred Drug-in-Adhesive Compositions of the Invention (W/W %)

| Material | Broad Range | Preferred Range |
|---|---|---|
| adhesive | 80-99 | 90-99 |
| permeation enhancer | 0-20 | 0-5 |
| Alzheimer pharmaceutical free Base | 0.1-20 | 0.5-10 |

2.5 The Protective Liner

The protective liner protects the adhesive layer until time of use and is peeled off before application of the patch to the patient and discarded. Preferred protective liners are of from about 0.5 mils to about 5 mils thick, preferably, 2 mils to 4 mils, occlusive, transparent fluoropolymer coated polyester film. The coating on this liner provides release from silicone skin contact adhesives, as well as, acrylate, polyisobutylene, and rubber-based adhesives. Suitable protective liners are well-known and commercially available, for example, Scotchpak 1022 Release Liner (3 mils thick), fluoropolymer coated polyester film, and other protective liners available from 3M Drug Delivery System, St. Paul, Minn.

3. Application Dosage and Delivery Rates of the Transdermal Patches of the Invention For treatment of Alzheimer's disease, dose size and frequency should be determined by a trained medical professional and will depend on many factors, including patient weight and disease severity. In general, the permeation rate of the Alzheimer's pharmaceutical by way of patches of the invention is such that blood-plasma levels are obtained in the patient that are comparable to blood-plasma levels obtained by the FDA approved oral version.

For example, Aricept™ (donepezil hydrochloride) is administered as once-daily tablets containing 5 mg or 10 mg of (corresponds to 4.56 mg or 9.12 mg of the freebase). PHYSICIAN'S DESK REFERENCE 1197 (59$^{th}$ ed., 2005). The elimination half life of donepezil is approximately 70 hours. PHYSICIAN'S DESK REFERENCE 1197 (59$^{th}$ ed., 2005).

In general, patches of the invention are applied for a period of one to seven days, depending on the severity of the disease and the patient's ability to remember to remove depleted patches and apply new ones. In general, more severely afflicted patients require patches of longer duration because of such patient's reduced ability to comply with treatment regimens. Patches of the invention are generally applied to either the patient's back (between shoulder blades), lower back, abdomen, chest, or upper arm, thigh region, preferably, applied to the upper chest.

The appropriate dosages and application locations are determined by a physician based on a variety of considerations. The rate at which the Alzheimer's pharmaceutical is absorbed is a function of skin permeability. Skin permeability varies between different sites on a patient's body and depends on the thickness of the stratum corneum. The stratum corneum is the outer-most layer of skin and is the main source of permeation and permeation resistance for dermally administered drugs. For example, the permeability, in general, increases in order from planter foot arch, lateral ankle, palm, ventral forearm, dorsal forearm, back, chest, thigh, abdomen, scalp, axilla, forehead, and scrotum; see R. C. Wester. & H. I. Maibach, *Regional variation in Percutaneous Absorption*, in PERCUTANEOUS ABSORPTION, MECHANISM, METHODOLOGY, DRUG DELIVERY 111-119 (R. L. Bronaugh & H. I. Maibach eds., 2nd ed. 1989), hereby expressly incorporated herein by reference.

The dosage of Alzheimer's pharmaceutical administered by way of patches of the invention is controlled by the active surface of the patch in contact with the skin. It is advantageous that several dosage strengths be available to the physician for his prescription, depending upon the disease severity. Thus, in general, a physician can adjust the Alzheimer's pharmaceutical dosage up or down by prescribing a patch having a larger or smaller active surface area.

Preferably, the overall average permeation rate of the Alzheimer's pharmaceutical from a patch of the invention is of from about 0.5 µg/cm$^2$/hr to about 20 µg/cm$^2$/hr, more preferably, of about from about 3 µg/cm$^2$/hr to about 13 µg/cm$^2$/hr. Preferably the average release rate in the first two hours after application is of from about 10 µg/cm$^2$/hr to about 250 µg/cm$^2$/hr, more preferably, of from about 25 µg/cm$^2$/hr to about 100 µg/cm$^2$/hr.

4. Preparation of Patches of the Invention

In general, patches of the invention are prepared as follows. The Alzheimer's pharmaceutical in free base form is added to 95% ethanol and stirred to dissolve the drug. Purified water was added to the ethanol-donepezil solution in amounts sufficient to generate a mixture containing 31.6 mg/g of donepezil in a 60% ethanol-water solvent. Two percent of hydroxyethylcellulose gelling agent was added to this solution slowly with stirring and mixed until a smooth gel was obtained (approximately one hour).

TABLE 4

Gel Reservoir Composition (W/W %) Donepezil TDS 1

| Material | W/W % |
|---|---|
| ethanol 95% (USP) | 60 |
| hydroxyethylcellulose | 2 |
| donepezil free base | 3 |
| water | balance |

A 0.05 mm thick contact adhesive layer of amine-resistant silicone medical adhesive (BIO PSA 7-4301, purchased from Dow Corning, Midland, Mich.) was coated on a fluorocarbon-treated polyester film by solution casting. A 0.05 mm thick rate-controlling membrane comprised of EVA (9% EVA) was pressure laminated to the exposed adhesive. The aqueous gel reservoir, prepared above, pouched between a standard 3M backing film (comprised of a multilaminate of polyethylene, polyester and EVA) and the release liner/adhesive/rate-controlling membrane on a heat-seal machine at a gel-loading of 30 mg/cm$^2$.

Sealed transdermal-delivery systems of the invention of 20 cm$^2$ were die cut and immediately pouched to avoid loss of ethanol. The pouched systems were allowed to equilibrate for at least two weeks in order to reach equilibrium concentration of the drug and ethanol in the rate-controlling membrane and adhesive layers.

5. Examples

5.1 High-Performance Liquid Chromatography (HPLC) Assay

The chromatograph (HPLC system) Hewlett-Packard Model 1090 Series II equipped with HP ChemStation software was used for the determination of donepezil concentrations. The analyses were carried out using Alltima Phenyl column (5 µm, 150×4.6 mm, Alltech Associates), methanol: 0.01 M sodium phosphate buffer at pH 6.9 (80:20) as the mobile phase, with a flow rate of 1 ml/min, at a wavelength of 315 nm, and injection volume of 10 µl. The nominal retention time for donepezil was 4.0 minutes. Calibration was carried out by the external standard method.

5.2 Example 1

Preparation of the Reservoir Patches of the Invention Depicted in FIG. 1 and not Having and Alzheimer's Pharmaceutical in the Adhesive Layer, Donepezil TDS 1

5.2.1 Preparation of Donepezil TDS 1, 20 cm$^2$ Patch Containing 18 Mg Donepezil/Patch, Amine-Resistant Silicone Medical Adhesive Transdermal Donepezil TDS 1 therapeutic systems according to FIG. 1 (rectangle with rounded edges, effective surface area of 20 cm$^2$) utilizing an aqueous ethanolic gel reservoir were prepared. Donepezil free base was added to 95% ethanol and stirred to dissolve the drug. Purified water was added to the ethanol-donepezil solution in amounts sufficient to generate a mixture containing 31.6 mg/g of donepezil in a 60% ethanol-water solvent. Two percent of hydroxyethylcellulose gelling agent was added to this solution slowly with stirring and mixed until a smooth gel was obtained (approximately one hour).

TABLE 5

Gel Reservoir Composition (W/W %) Donepezil TDS 1

| Material | W/W % |
|---|---|
| ethanol 95% (USP) | 60 |
| hydroxyethylcellulose | 2 |
| donepezil free base | 3 |
| water | balance |

A 0.05 mm thick contact adhesive layer of amine-resistant silicone medical adhesive (BIO PSA 7-4301, purchased from Dow Corning, Midland, Mich.) was coated on a fluorocarbon-treated polyester film by solution casting. A 0.05 mm thick rate-controlling membrane comprised of EVA (9% EVA) was pressure laminated to the exposed adhesive. The aqueous gel reservoir, prepared above, pouched between a standard 3M backing film (comprised of a multilaminate of polyethylene, polyester and EVA) and the release liner/adhesive/rate-controlling membrane on a heat-seal machine at a gel-loading of 30 mg/cm$^2$.

Sealed transdermal-delivery systems of the invention of 20 cm$^2$ were die cut and immediately pouched to avoid loss of ethanol. The pouched systems were allowed to equilibrate for at least two weeks in order to reach equilibrium concentration of the drug and ethanol in the rate-controlling membrane and adhesive layers.

5.2.2 Preparation of Donepezil TDS 2, 20 cm$^2$ Patch Containing 18 mg Donepezil/Patch, Polyisobutylene with Mineral Oil Contact Adhesive Transdermal Donepezil TDS 2 therapeutic systems according to FIG. 1 (rectangle with rounded edges, effective surface area of 20 cm$^2$) utilizing an aqueous ethanolic gel reservoir were prepared. Donepezil free base was added to 95% ethanol and stirred to dissolve the drug. Purified water was added to the ethanol-donepezil solution in amounts sufficient to generate a mixture containing 31.6 mg/g of donepezil in a 60% ethanol-water solvent. Two percent of hydroxyethylcellulose gelling agent was added to this solution slowly with stirring and mixed until a smooth gel was obtained (approximately one hour).

TABLE 6

Gel Reservoir Composition (W/W %) Donepezil TDS 2

| Material | W/W % |
|---|---|
| ethanol 95% (USP) | 60 |
| hydroxyethylcellulose | 2 |
| donepezil free base | 3 |
| water | balance |

The adhesive polyisobutylene with mineral oil was prepared by adding low-molecular weight polyisobutylene (average molecular weight 35,000) and high-molecular weight polyisobutylene (average molecular weight 1,200,000) to a stirring vessel in a respective ratio of 1.25:1.0. Light mineral oil was added to the vessel in a ratio of about 0.8 to 1 part of the above polyisobutylene mixture. Sufficient heptane was added to the vessel to dissolve the above-mixture. This polyisobutylene adhesive mixture was coated on a fluorocarbon-treated polyester film by solution casting at a thickness of 0.05 mm.

A 0.05 mm thick rate-controlling membrane comprised of EVA (9% EVA) was pressure laminated to the exposed adhesive. The aqueous gel, prepared above, pouched between a standard 3M backing film (comprised of a multilaminate of polyethlene, polyester and EVA) and the release liner/adhesive/rate-controlling membrane on a heat-seal machine at a gel-loading of 30 mg/cm$^2$. The drug loading is 0.9 mg donepezil per cm$^2$.

Sealed transdermal-delivery systems of the invention of 20 cm$^2$ were die cut and immediately pouched to avoid loss of ethanol. The pouched systems were allowed to equilibrate for at least two weeks in order to reach equilibrium concentration of the drug and ethanol in the rate controlling and adhesive layers.

5.2.3 Quantitative Analysis of Donepezil TDS 1 and Donepezil TDS 2

The donepezil content in the Donepezil TDS 1 and Donepezil TDS 2 patches was determined as follows. Each patch was cut into half, the protective liner was removed and the severed patch placed in a 60-ml clear glass jar. Then 40 ml methanol was added, the jar tightly capped and placed on a wrist-action shaker for overnight to extract the donepezil completely from the patch. The donepezil concentration in the methanol extract was quantified by HPLC.

The quantization of donepezil in Donepezil TDS 1 and Donepezil TDS 2, was carried out by reversed-phase high-performance liquid chromatography as described above.

5.2.4 Comparison of Permeation Rate in Human Cadaver Skin Of Donepezil TDS 1 vs Donepezil TDS 2

In vitro skin permeation was performed on Donepezil TDS 1 and Donepezil TDS 2 prepared above to demonstrate that both transdermal products deliver at a designed permeation rate for a period of one to seven days.

A system employing six improved Franz diffusion cells with a diffusional area of 1.767 cm$^2$ (FDC-400, Crown Glass Company, Somerville, N.J.) were used for the permeation studies. The receptor phase volume was 12 ml for Franz diffusion cells. The receptor temperature was maintained at 37° C. with a water jacket. Phosphate Buffered Saline (PBS buffer) pH 7.4 was used as a receptor medium. Human cadaver skin dermatomed at 375 µM (New York Firefighters Skin Bank, New York, N.Y.) was hydrated at room temperature in normal saline solution for 15 minutes. The skin sample was mounted onto the receptor compartment. Donepezil TDS 1 or Donepezil TDS 2 was placed on the stratum corneum side of the skin. The donor cap was then placed onto the patch and clamped with the receptor compartment (dermal side in contact with the receptor medium).

Figure 3:
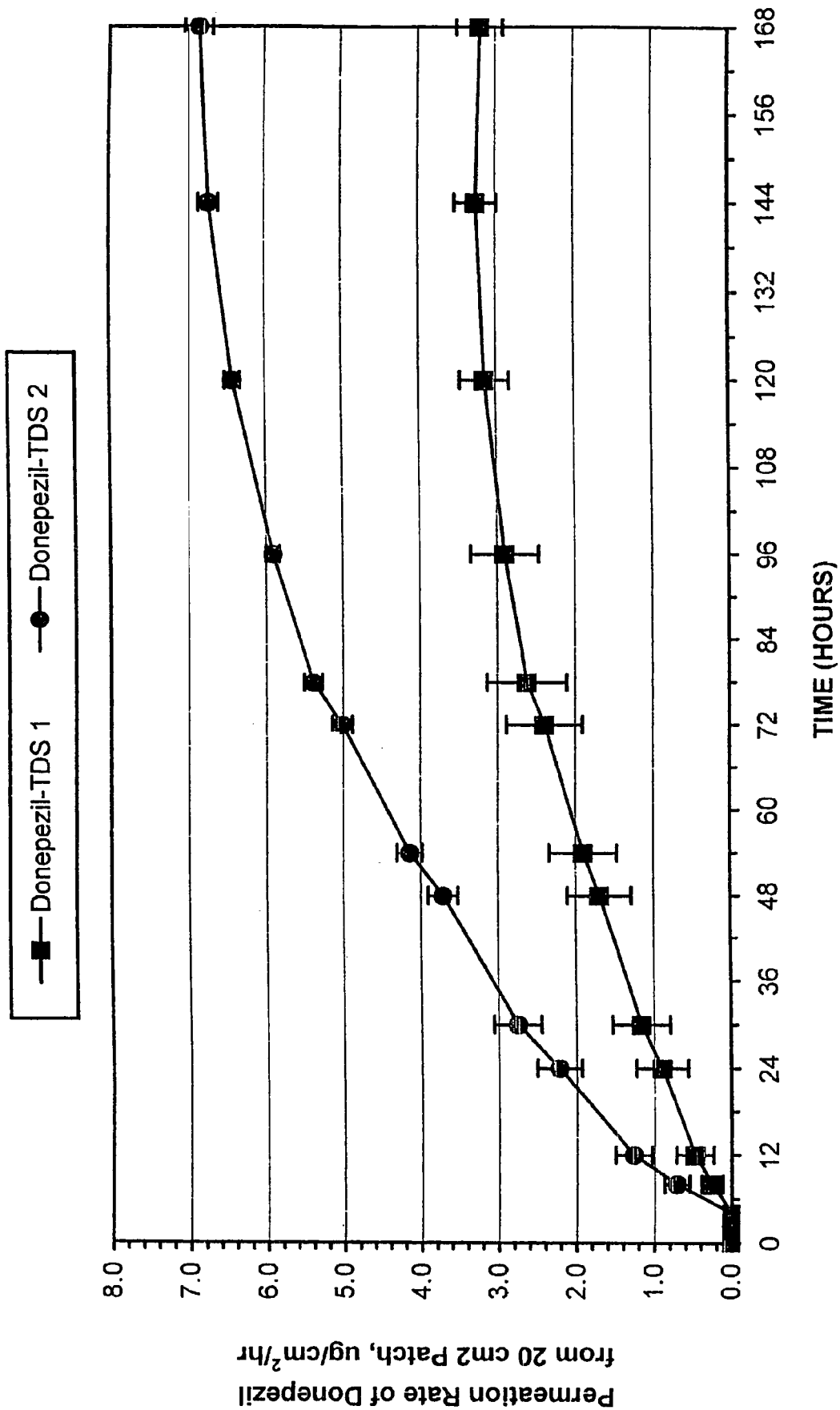
FIG. 3 depicts the permeation rate of donepezil through human cadaver skin versus time for a reservoir patch of the invention.

Samples were withdrawn periodically as shown on FIG. 3 up to 168 hours and analyzed for donepezil concentration by HPLC. The permeation rate of donepezil was plotted against time. FIG. 3 depicts donepezil permeation rates versus time for Donepezil TDS 1 and Donepezil TDS 2. Average skin-permeation rate for Donepezil TDS 1 was 3.20 µg/cm$^2$/hr and the average skin-permeation rate for Donepezil TDS 2 was 6.85 µg/cm$^2$/hr.

5.2.5 Comparison of in Vitro Release of Donepezil TDS 1 vs Donepezil TDS 2

To assure that Donepezil TDS 1 and Donepezil TDS 2 release the drug at designed rate for a period of 3 to 7 days, in vitro release was performed as described in USP 28, Apparatus 5—paddle over disk method. Vanderkemp 600 six spindles dissolution unit was in these studies. Sodium phosphate buffer (0.01 M) pH 5.8 was used as a dissolution medium and was maintained at 32° C. Transdermal patch was applied on stainless screen support assuring that release surface side up and the system is as flat as possible at the bottom of the vessel.

Figure 4:
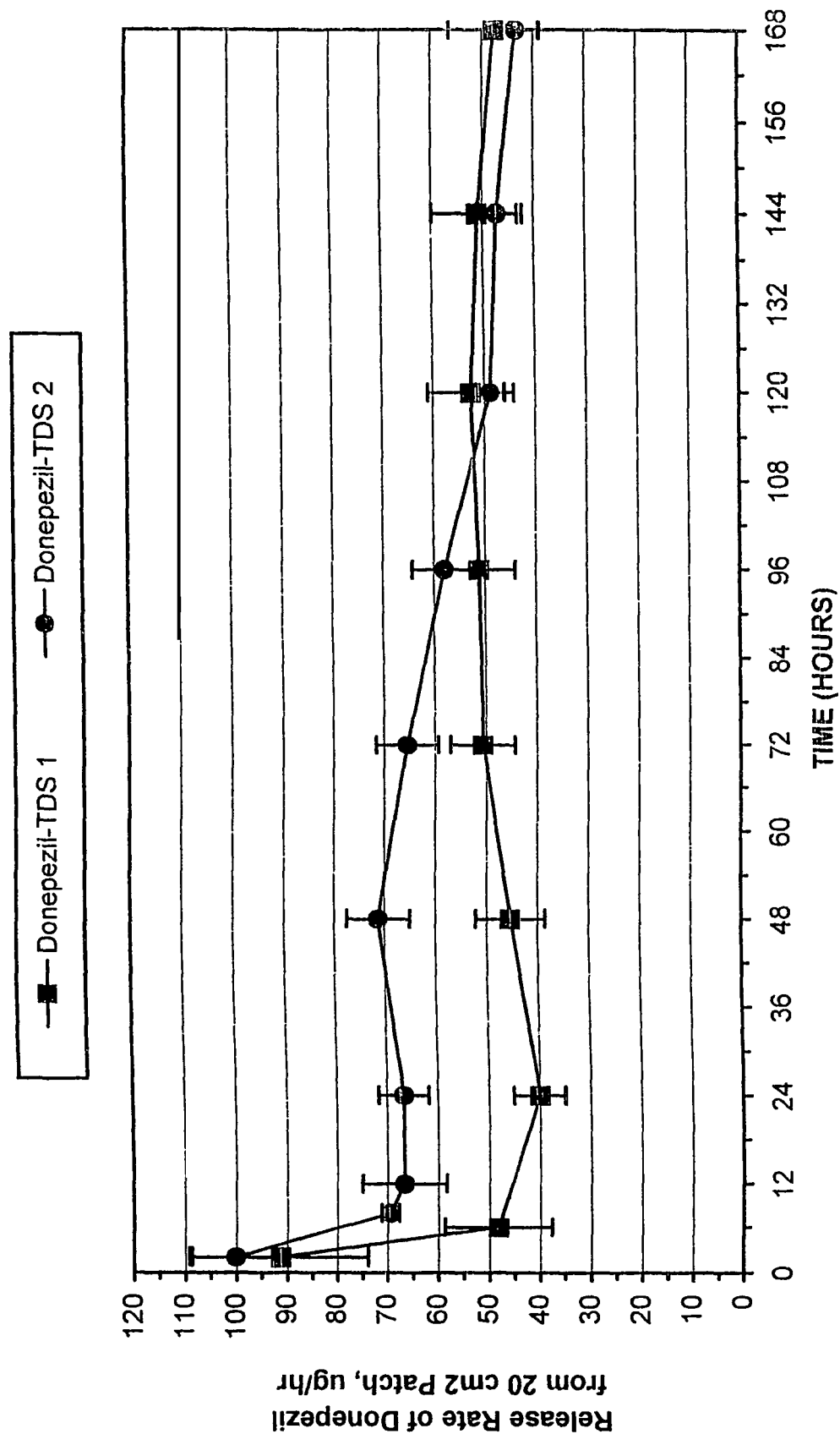
FIG. 4 depicts the release rate of donepezil versus time for a reservoir patch of the invention.

Samples were withdrawn periodically as shown on FIG. 4 up to 168 hours and analyzed for donepezil concentration by HPLC. FIG. 4 depicts the donepezil release rate versus time for Donepezil TDS 1 and Donepezil TDS 2. The average release rate for Donepezil TDS 1 was 47.6 µg/hr, and the average release rate for Donepezil TDS 2 was 43.5 µg/hr.

5.3 Example 2

Preparation and Testing of Drug-in-Adhesive Type Patches of the Invention Depicted in FIG. 2

Donepezil (200 mg) and 16 g of a solution comprising 60% by weight of amine-resistant silicone medical adhesive in ethyl acetate (BIO PSA 7-4302, from Dow Corning, Midland, Mich.) were accurately weighed into a 60-ml glass bottle, vortexed for 5 minutes and mixed on a tilting bottle roller. The mixing was carried out for 24 hours in order to ensure thorough mixing of the drug in the adhesive. Thus a 2% W/W % of drug in adhesive is obtained. The drug loading is 0.3 mg donepezil per cm$^2$.

The drug-loaded adhesive mixture prepared above was coated along the length of a Scotchpak 1022 (3M) release liner using a Werner-Mathis table-top coater at 100 µm gap. The coated release liner was dried in an oven at 80° C. for 10 minutes. The dried, coated release liner was laminated with Scotchpak 1220 (3M) backing material. The final matrix (drug-in-adhesive) patch was die cut into smaller patches with a surface area of 5 cm$^2$ in size.

5.3.1 Determination of Donepezil Content and Coating Weight in the 5 cm$^2$ Drug-In-Adhesive Patch Prepared Above The donepezil content in the matrix, drug-in-adhesive patches prepared above was determined as follows. The patch's release liner was peeled off. Then the drug-in-adhesive matrix with backing material was placed in a 20-ml scintillation vial. A solvent (10 ml), such as methanol or ethyl acetate, was added to the vial to extract donepezil from the patch. The vial was tightly capped and placed on a wrist-action shaker overnight in order to extract the drug completely from the adhesive matrix. The drug concentration in the extract was evaluated by HPLC using method previously described.

5.3.2 Human Cadaver Skin-Permeation Studies of the 5 cm$^2$ Drug-In-Adhesive Patch Prepared Above In vitro skin permeation was performed on 5 cm$^2$ drug-in-adhesive patch prepared above to demonstrate high initial release rate of donepezil though human caver skin.

Valia-Chien (VC) diffusion cells with a diffusional area of 0.6263 cm$^2$ (VC-100, Crown Glass Company, Somerville, N.J.) were used for the permeation studies. Human cadaver skin, dermatomed at 375 µM (New York Firefighters Skin Bank, New York, N.Y.), was hydrated at room temperature in normal saline solution for 15 minutes. The skin sample was mounted between the donor and receptor compartments, the patch was placed on the stratum corneum side of the skin and clamped with the receptor compartment (dermal side in contact with the receptor medium). The receptor phase volume was 4 ml. The receptor temperature was maintained at 37° C. with a water jacket. Phosphate Buffered Saline (PBS buffer) pH 7.4 was used as a receptor medium. Samples were withdrawn periodically and analyzed for donepezil concentration by HPLC. The skin permeation rate over 24 hours was about 10.2 µg/cm$^2$/hr.

5.4 Example 3

Preparation of a Reservoir Patches of the Invention Depicted in FIG. 1 Comprising an Alzheimer's Pharmaceutical in Both the Reservoir and in the Adhesive Layer Transdermal Donepezil TDS 3 therapeutic systems according to FIG. 1 (rectangle with rounded edges, effective surface area of 40 cm$^2$) utilizing an aqueous ethanolic gel reservoir are prepared with donepezil in both the drug reservoir and in the adhesive layer.

In this example of patches of the invention, both the drug reservoir and the adhesive layer will comprise donepezil. In such a patch of the invention, there is an increase in the initial release rate (burst effect). This reduces the lag time for influx of the drug into the patient's blood stream upon application to the patient's skin. In addition, having the drug in the drug reservoir provides a constant transdermal delivery of drug throughout the 3 to 7 day application period comparable to the oral dosage.

Donepezil free base is added to 95% ethanol and stirred to dissolve the drug. Purified water is added to the ethanol-donepezil solution in amounts sufficient to generate a mixture containing 31.6 mg/g of donepezil in a 60% ethanol-water solution. Two percent of hydroxyethylcellulose gelling agent is added to this solution slowly with stirring and mixed until a smooth gel is obtained (approximately one hour).

TABLE 9

| Gel Reservoir Composition (W/W %) Donepezil TDS 1 | |
| --- | --- |
| Material | W/W % |
| ethanol 95% (USP) | 60 |
| hydroxyethylcellulose | 2 |
| donepezil free base | 3 |
| water | balance |

Donepezil (200 mg) and 16 g of a solution comprising 60% by weight of amine-resistant silicone medical adhesive in ethyl acetate (BIO PSA 7-4302, from Dow Corning, Midland, Mich.) are accurately weighed into a 60-ml glass bottle, vortexed for 5 minutes and mixed on a tilting bottle roller. The mixing is carried out for 24 hours in order to ensure thorough mixing of the drug in the adhesive. Thus a 2% W/W % of drug in adhesive is obtained.

The drug-loaded adhesive mixture above is coated along the length of a Scotchpak 1022 (3M) release liner using a Werner-Mathis table-top coater at 100 µm gap. The coated release liner is dried in an oven at 80° C. for 10 minutes.

A 0.05 mm thick rate-controlling membrane comprised of EVA (9% EVA) is pressure laminated to the exposed drug-in-adhesive layer. The aqueous gel reservoir, as can be prepared above, is pouched between a standard 3M backing film (comprised of a multilaminate of polyethylene, polyester and EVA) and the release liner/drug-in-adhesive/rate-controlling membrane on a heat-seal machine.

The above transdermal-delivery systems are die cut to 40 cm$^2$ and immediately pouched to avoid loss of ethanol. The pouched systems are allowed to equilibrate for at least two weeks in order to reach equilibrium concentration of the drug and ethanol in the rate-controlling membrane. In the donepezil TDS 3 so prepared, the drug loading of the gel reservoir is 0.9 mg/cm$^2$, and the drug loading in the drug-in-adhesive layer is 0.3 mg/cm$^2$, thus, the total drug loading is 1.2 mg donepezil per cm$^2$.

In the 40 cm$^2$ Donepezil TDS 3 so prepared, the first two-hour release rate is about 25 µg/cm$^2$/hr to about 100 µg/cm$^2$/hr. The average release rate of the Donepezil TDS 3 over 7 days is about 5 µg/cm$^2$/hr to about 20 µg/cm$^2$/hr.

5.5 Example 4

Treatment of Alzheimer's In a Patient

A 70 year old male, weighing 160 lbs is diagnosed with moderate Alzheimer's disease. The patient is otherwise in good health. The upper torso is clipped to remove hair and cleaned with soap and water. The release liner of 40 cm$^2$ transdermal delivery system donepezil TDS 3 as prepared in Example 3 is removed and the patch applied to the upper torso by a caretaker. A new patch is applied as above every four days. The patient is monitored regularly by the treating physician.

The present invention is not to be limited in scope by the specific embodiments disclosed in the examples, which are intended as illustrations of a few aspects of the invention. Any embodiments that are functionally equivalent are within the scope of this invention. Indeed, various modifications of the invention in addition to those shown and described herein will become apparent to those skilled in the art and are intended to fall within the scope of the appended claims. All cited references are hereby incorporated herein in their entireties by reference.

What is claimed is:

1. A patch for transdermal delivery of donepezil, comprising a backing film and a matrix type adhesive, wherein the matrix type adhesive consists essentially of (1) a free-base form of donepezil; (2) an adhesive material fabricated from one or more polymers selected from the group consisting of polyisobutylene, silicone and polyacrylate; and (3) a skin permeation enhancer selected from the group consisting of linoelic acid, lauryl lactate, lauryl alcohol, monofunctional glycerides, and combinations thereof.

2. The patch of claim 1, wherein the silicone is an amine-resistant silicone.

3. The patch of claim 1, wherein the polyacrylate is selected from the group consisting of polybutylacrylate, polymethylacrylate, poly-2-ethylhexyl acrylate, and combinations thereof.

4. The patch of claim 1, which delivers the donepezil through the skin at a rate of about 3 μg/cm$^2$/hr to about 13 μg/cm$^2$/hr.

* * * * *